United States Patent [19]

Ouchi et al.

[11] 4,261,343
[45] Apr. 14, 1981

[54] ENDOSCOPE

[76] Inventors: Teruo Ouchi, Kamifukuoka; Hirohisa Ueda; Kazukiyo Tamada, both of Tokyo, all of Japan

[21] Appl. No.: 24,214

[22] Filed: Mar. 26, 1979

[30] Foreign Application Priority Data

| Mar. 28, 1978 [JP] | Japan | 53-39814[U] |
| Mar. 28, 1978 [JP] | Japan | 53-39815[U] |
| Mar. 31, 1978 [JP] | Japan | 53-41966[U] |
| May 15, 1978 [JP] | Japan | 53-64797[U] |

[51] Int. Cl.$^3$ ............................................. A61B 1/00
[52] U.S. Cl. ...................................................... 128/4
[58] Field of Search ......................................... 128/3–8, 128/274, 276–277, 278

[56] References Cited

U.S. PATENT DOCUMENTS

| 3,726,272 | 4/1973 | Fukami et al. | 128/6 |
| 3,730,645 | 5/1973 | Mashakaru et al. | 128/278 X |
| 3,903,877 | 9/1975 | Terada | 128/6 |
| 3,958,566 | 5/1976 | Furihata | 128/4 |

Primary Examiner—John D. Yasko

[57] ABSTRACT

An air and water supplying device for an endoscope, having air supplying tubes connecting an air pump and an endoscope provided with an air and water switching valve. A water storing tank is provided with a compressed air receiving inlet and a cleaning water delivering outlet, and a water supplying tube connects the endoscope and the water supplying tank to supply air and water to the top end part of said endoscope. An inlet receives the compressed air in the air pump in a water supplying path made up of the water supplying tube and a water pumping-up tube in the water storing tank in such a manner that the particular inlet is normally closed by an operating valve mechanism provided therefore. When the particular inlet is opened by the operating valve mechanism, the compressed air introduced into the particular inlet causes to discharge the water left in the water supplying path. The air and water switching valve, in three embodiments also provides positive switching without contaminating feed back while eliminating the second valve mechanism. Selective air pressure application is achieved by means of an air regulator employed in the cylinder and adjustable by rotation of the piston. Suction control independent of operator finger position on the piston is also provided to achieve variable suction rates dependent on the amount of piston depression.

7 Claims, 16 Drawing Figures

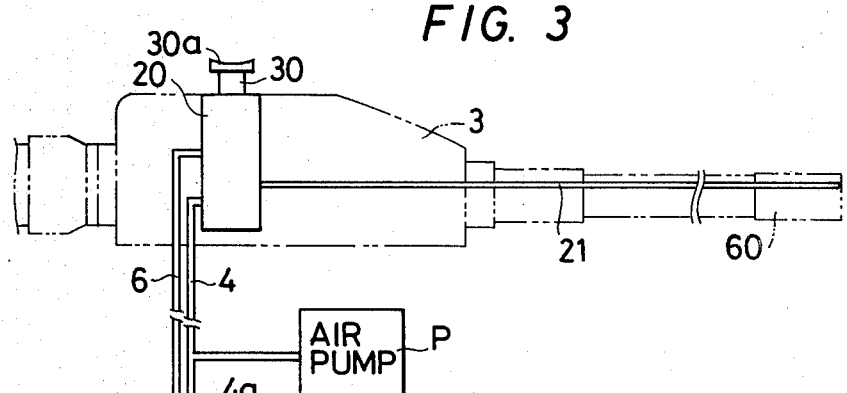
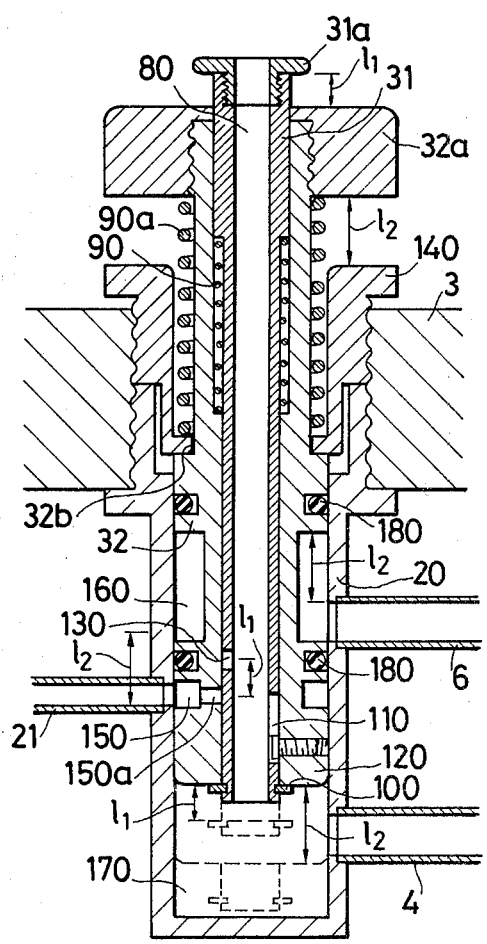

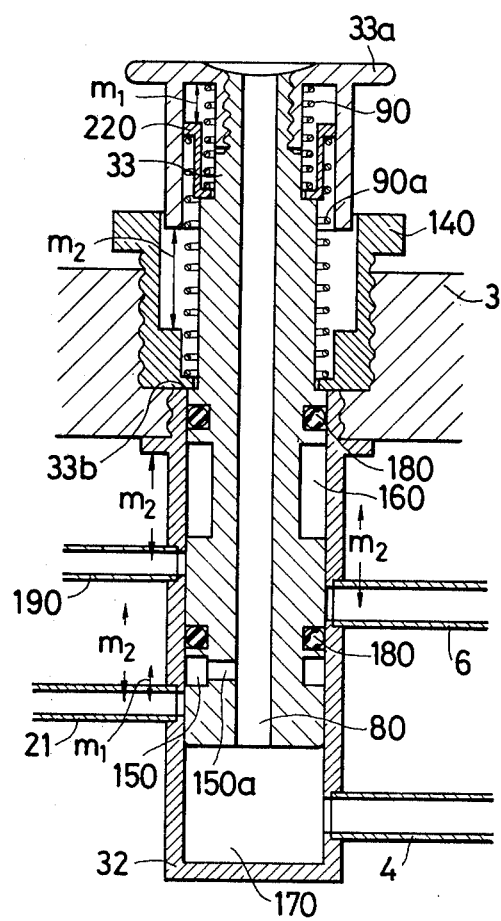

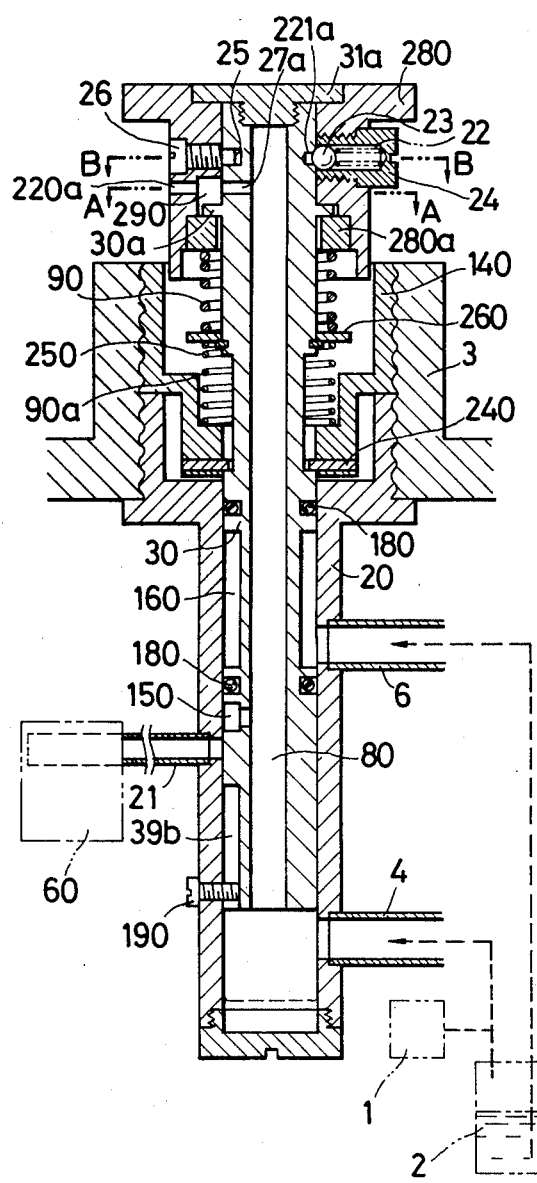

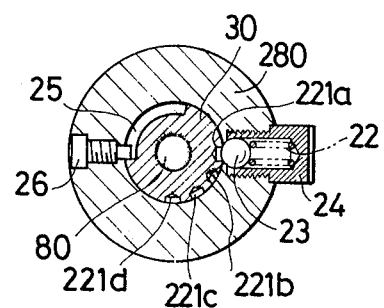
FIG. 11
FIG. 12
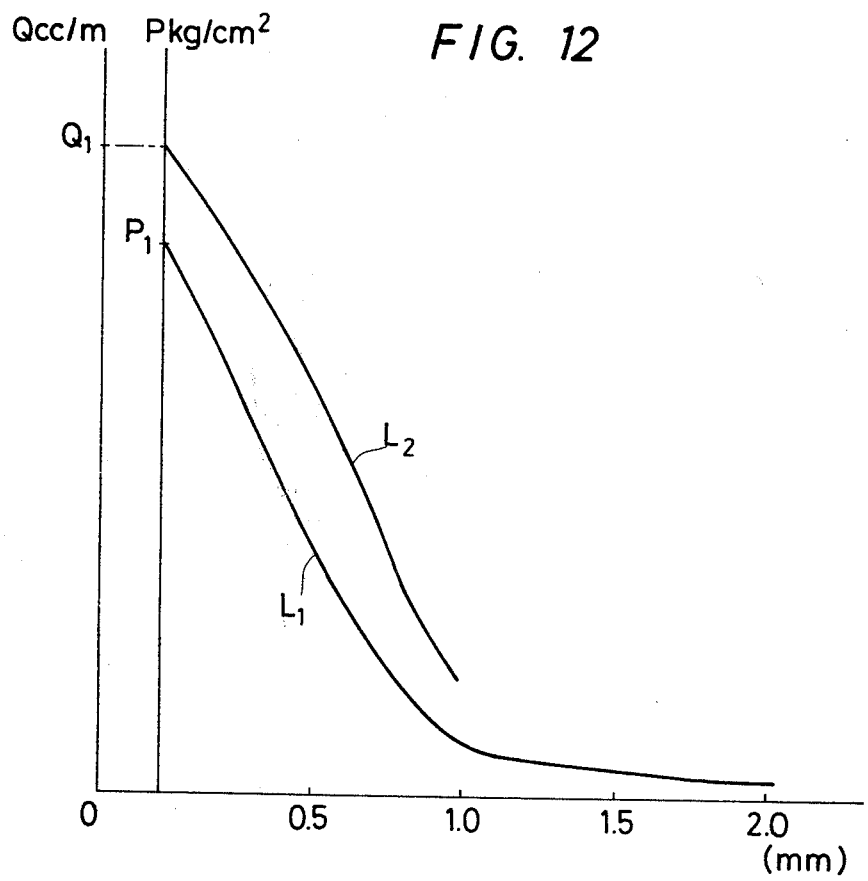

ENDOSCOPE

BACKGROUND OF THE INVENTION

This invention relates to air and water supplying devices for endoscopes, and more particularly to an air and water supplying device capable of discharge the water left in a water supplying path connected between a cleaning water storing tank and an endoscope and in a water supplying tube within the endoscope.

An endoscope, especially an endoscope for examining the digestive organs, is used to observe a portion of the body cavity through the window at the top end part of a flexible elongated pipe of the endoscope inserted into the body cavity. It is necessary to suitably inflate the portion to be examined by supplying air in order to provide an observing distance between the body portion to be examined and the top end part of the endoscope. Furthermore, a supply of water must be provided at the portion to be examined in order to clean the lens in the window provided at the top end part of the endoscope, or to remove dirt from the window, or to clean the portion to be observed.

For this purpose, the endoscope of this type is provided with an air and water supplying mechanism in which an air supplying tube and a water supplying tube connected to the manual operating section of the endoscope are connected through a supply air and water switching valve mechanism to an air and water supplying tube. The supply tube extends through the flexible pipe of the endoscope to the top end part so that air or water can be suitably supplied to the portion to be examined while the endoscope is being operated.

If the use of such a conventional endoscope is suspended immediately after water has been supplied hereto, the cleaning water is left in the water supplying path of the water supplying system thereof after the examination. It is very difficult to remove the water left in the water supplying tube which extends from the water storing tank to the endoscope. The end portion of the air and water supplying tube opened at the top end of the endoscope is contaminated by the water which is caused to flow backwardly into the tube by the internal pressure of the body. Furthermore, the water left in the water supplying system is liable to be spoiled. Accordingly, it is not sanitary to use the endoscope again with any water remaining in the water supplying system. The water supplying system is made up of plastic tubes. Because of the water absorbing characteristic of the plastic tube and the corrosion of the connections of the water supplying system, water may also leak out of the water supplying system.

In order to observe a portion of the body cavity to be examined with an endoscope, it is necessary to inflate the portion to be examined to a certain extent. For this purpose, the air pump is provided for the endoscope. The air supplying pressure of the air pump is relatively high, because it is utilized also for supplying water to clean the observing window of the endoscope.

With a conventional air supplying means, the period of time during which air is supplied into the body cavity by the air pump is controlled to adjust the quantity of air supplied into the body cavity. However, in such an air supplying quantity controlling method, air is supplied under a pressure much higher than the pressure which a portion of the body cavity to be examined can withstand. Therefore, the excessively high pressure may cause extreme discomfort to a patient and may rupture the body cavity.

Depending on portions of the body cavities to be examined such as the stomach, the esophagus and the duodenum, the necessary quantity of air to be supplied thereinto is different. However, in conventional methods, the same quantity of air is supplied thereinto. As a result, the observing conditions of these portions having different conditions of walls thereof are varied, and the images formed by the endoscope are therefore varied, which may result in errors in the diagnoses.

In the diagnosis by observing a portion to be examined with an endoscope for a correct diagnosis it is essential to variously change the condition of expansion of the portion to dynamically observe it. However, with air supplying means of the conventional device, it is very difficult to control the air supplying quantity for dynamically observing the conditions of expansion of the portion to be examined.

The operation of an endoscope is carried out by delivery of cleaning water to a portion of the body cavity to be examined to remove mucus, etc. from the observing window of the endoscope or to clean the portion to be examined so that the portion to be examined can be sufficiently observed. The cleaning water used in this operation and the mucus in the body cavity should be forcibly discharged out of the body by using a suction mechanism.

For this purpose, heretofore, the suctions mechanism of this type comprises a suction pump which is operated by a power device and is connected to a suction pipe opened in the top end part of the endoscope. The suction operation of the suction mechanism is carried out intermittently during observation. Since the suction pump cannot start instantaneously, the power device is maintained in operation during the observation so that the suction pump operates instantaneously to meet the requirement of suction. During the ordinary operating time, the suction pressure of the suction pump is reduced or eliminated by suction air from an air passing pipe which is opened in the finger placing surface of a piston protruding from the manual operating section body of the endoscope. When suction is required, the finger is placed on the finger placing surface of the piston to depress the latter. In this operation, the air passing pipe opened in the finger placing surface is closed by the finger, and therefore the suction pressure of the suction pump is increased. As a result, the cleaning water or the like is discharged through the sucking pipe.

The conventional device as described above is advantageous in that the suction is effected instantaneously merely by placing the finger on the top of the piston. However, it is still disadvantageous for the following reasons. If, during the operation of the endoscope, the operator is enthusiastic for the observation or the operation of the endoscope, he may inadvertently place his finger on the top of the piston to close the air passing pipe to unnecessarily suck out matter in the body cavity. Furthermore, in order to avoid this unnecessary suction, he has to keep his finger off the top of the piston intentionally, which leads to fatigue.

As mentioned, in observing for instance a portion of the stomach with an endoscope, it is necessary to send air thereinto to provide an observing distance between the endoscope and the portion to be examined, or to inflate the body cavity. With an endoscope provided with the above-described prior art air supplying device and suction device, the conditions of a portion to be examined can be dynamically observed during the process in which, after air is supplied into the body cavity by the air supplying device to excessively expand the portion to be examined and the air is gradually removed from the body cavity by the suction device. The conventional suction device is operated by closing the end of the air passing pipe with the finger, but it is difficult to suitably adjust the degree of suction with the sensual operation of the finger. Thus, the conventional device is not practical.

SUMMARY OF THE INVENTION

Accordingly, an object of this invention is to provide an air and water supplying device in which after the use of an endoscope, the water left in the water supplying system can be positively discharged by the utilization of compressed air pressure used to supply air to the endoscope.

Another object of this invention is to provide an endoscope that is sanitary and easy to use.

Yet another object of this invention is to provide a switching device in which when no air is supplied through an air supplying conduit pipe communications to the top end part of an endoscope, the air supplying conduit pipe is disconnected from an air discharging path, and the outer end of the conduit pipe is maintained closed, and in supplying water, a compressed air discharging path is disconnected from the air supplying system.

Still another object of this invention is to provide air and water supplying device for an endoscope, in which in supplying air into the body cavity, the air supplying pressure and the air supplying quantity per unitary time are suitably controlled.

A further object of this invention is to provide a device to protect a patient from danger due to an excessively high pressure and to dynamically observe the conditions of expansion of a portion of the body cavity to be examined.

An additional object of this invention is to provide a suction device for an endoscope, in which instead of closing the end of the air passing pipe with the finger, the suction is controlled by the depression of a piston having excellent operating stability.

Another additional object of this invention is to provide a suction device where the degree of suction is readily adjusted by the depression of the piston.

These and other objects of this invention will become apparent from the drawings and the description of the preferred embodiments that follow.

BRIEF DESCRIPTION OF THE DRAWINGS

FIG. 3 is an explanatory diagram showing the arrangement of a third example of a device for switching air and water supplying operations in an endoscope according to this invention;

FIG. 4 is a vertical sectional view showing the essential components of a first example of the air-water valve according to the invention;

FIG. 5 is a vertical sectional view showing the essential components of a second example of the air-water valve according to the invention;

FIG. 6 is a vertical sectional view showing the essential components of a third example of an air and water supplying device according to this invention;

FIGS. 7 through 10 are sectional views taken along line A—A in FIG. 6, showing the conditions of adjustment of outlets formed in a piston shown in FIG. 6;

FIG. 11 is a sectional view taken along line B—B in FIG. 6, showing an adjustment position holding mechanism;

FIG. 12 is a graphical representation indicating the characteristic curves representative of adjusted air supplying pressures and air supplying quantities;

DESCRIPTION OF THE PREFERRED EMBODIMENTS

Figure 1:
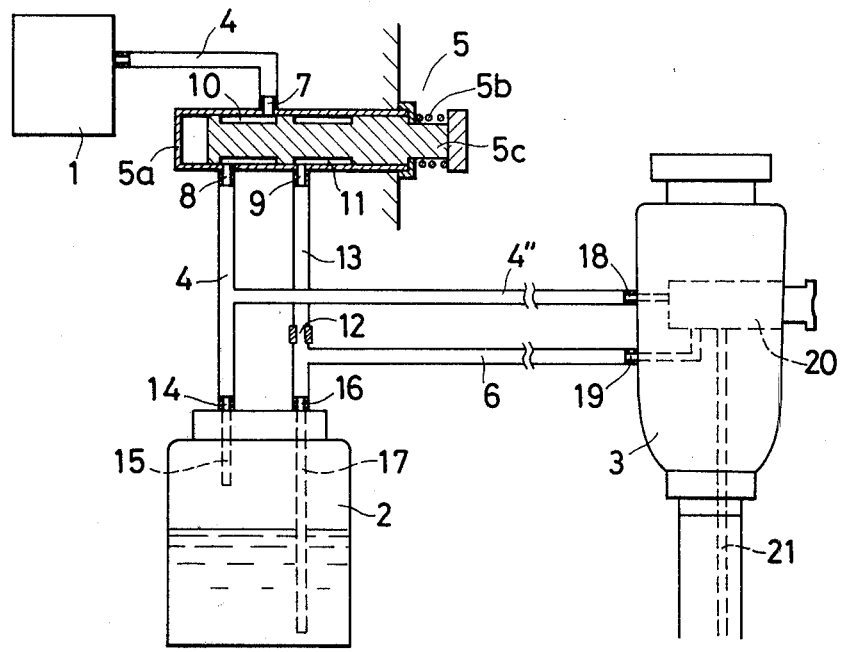
FIG. 1 is an explanatory diagram showing the arrangement of a first example of an air and water supplying device according to this invention.

This invention will be described with reference to its preferred embodiments shown in the accompanying drawings. FIG. 1 is an explanatory diagram showing the arrangement of one example of an air and water supplying device according to the invention. As shown in FIG. 1, an air pump 1 is connected through an air supplying tube 4 to a cleaning water storing tank 2 and an endoscope 3. A supply path switching valve 5 is interposed in the tube 4 between elements 4 and 4'. On the other hand, the water storing tank 2 is connected through a water supplying tube 6 to the endoscope 3.

The supply path switching valve 5 comprises: a cylinder housing 5a secured to the wall of the housing of the air pump 1, and a piston 5c, fitted in the housing 5a in such a manner that it is energized outwardly by the elastic force of a spring 5b. The housing 5a has a supply air receiving inlet 7, and first and second supply air delivering outlets 8 and 9 in association with the inlet 7. The piston 5c has a first circumferential groove 10 which communicates the inlet 7 with the first outlet 8 when the piston is moved outward of the cylinder and a second circumferential groove 11 which communicates the inlet 7 with the second outlet 9 when the piston is moved to an inward position.

The second supply air delivering outlet 9 is connected to the middle portion of the water supplying tube 6 through a check valve 12 and an air supplying tube 13 for discharging water. In FIG. 1, the following other elements are shown. Reference numeral 14 designates the supply air receiving inlet of the water storing tank 2 and reference numeral 15 is an air supplying tube opened in the tank 2. The water supplying outlet of the tank 2 is designated 16 and is coupled to a water pumping-up tube 17 that opens in the tank 2. The supply air receiving inlet 18 of the endoscope 3 and the supply water receiving inlet 19 of the endoscope 3 are coupled to a supply air and water switching valve 20. Reference numeral 21 designates an air and water supplying tube coupled to the valve 20.

Figure 2:
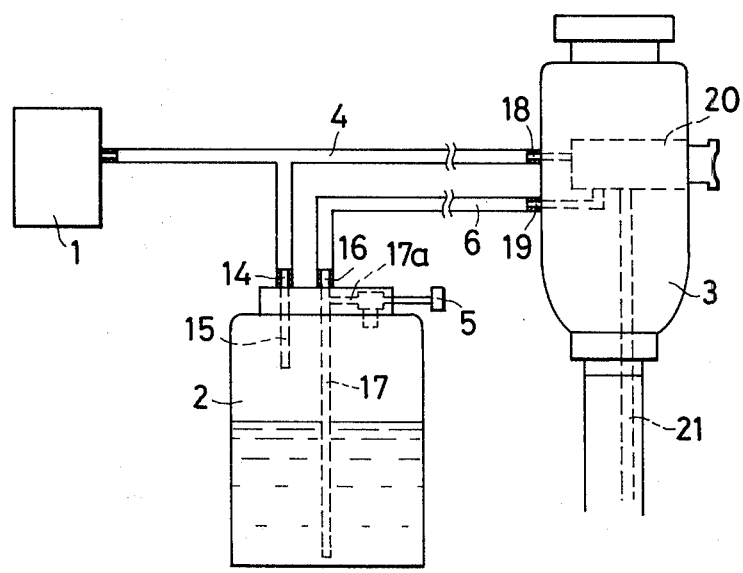
FIG. 2 is also an explanatory diagram showing the arrangement of a second example of the air and water supplying device according to the invention.

FIG. 2 shows a second example of the air and water supplying device according to the invention, in which those components which have been previously described with reference to FIG. 1 have therefore been similarly numbered. The water pumping-up tube 17 opened in the tank 2 is provided with a branch tube 17a in the upper portion of the tank 2 where air exists (hereinafter referred to as "a hollow part" when applicable), in such a manner that the branch tube 17a is opened or closed in the hollow part of the tank by operating a valve 5.

In the first example of the air and water supplying device constructed as shown in FIG. 1, under the normal operating condition the piston 5c of the supply path switching valve 5 is extended outwardly as shown in FIG. 1. Under this condition, the compressed air in the pump 1 is delivered to the endoscope 3 and the tank 2 through the first air supplying tube 4, the supply air receiving inlet 7, the circumferential groove 10, the supply air delivering outlet 4', and the second air supplying tube 4" which is connected to the endoscope and the tank. If, in this case, the supply air and water switching valve in the endoscope 3 is in the air supplying state; that is, the water supplying side thereof is closed, then under the condition that the delivery of air to the tank 2 is blocked, the compressed air from the air pump 1 is delivered to the top end part of the endoscope through the air and water supplying tube 21.

If, under this condition, the air supplying side is closed and the water supplying side is opened by operating the supply air and water switching valve 20, then the compressed air from the air pump 1 is delivered into the water storing tank 2. As a result, a pressure is created in the tank 2, whereby the water in the tank 2 is pressurized. Accordingly, the water is forcibly delivered through the water pumping-up tube 17, the water supplying tube 6 and the air and water supplying tube 21 to the end portion of the endoscope.

After a portion of the body cavity has been examined with the endoscope with the aid of the above-described air and water supplying operation, the piston 5c of the supply path switching valve 5 is depressed against the elastic force of the spring 5b. In this operation, as the piston 5c is moved inwardly, the supply air receiving inlet 7 communicates with the second supply air delivery outlet 9 through the circumferential groove 11, so that the compressed air in the air pump 1 is delivered through the air supplying tube 13 for discharging water to the water supplying tube 6. As a result, the water left in the water supplying system including the air and water supplying tube is discharged from the top end part of the endoscope through the tube 6. The supply air and water switching valve 20 has been placed in the water supplying state during this operation.

In the second example of the air and water supplying device shown in FIG. 2, the air and water supplying operation can be performed in a similar manner to the first example shown in FIG. 1, with the branch tube 17a in the water storing tank 2 closed by operating the valve 5. If the branch tube 17a is opened in the hollow part of the water storing tank 2 by operating the valve 5 after the examination of a portion of the body cavity with the endoscope, then the compressed air delivered into the water storing tank 2 from the air pump 1 is delivered to the water pumping-up tube 17. As a result, the water left in the water supplying system including the tube 17 is discharged from the tip end of the air and water supplying tube in the top end part of the endoscope through the supply air and water switching valve 20.

As is apparent from the above description, the air and water supplying device according to the invention is a simple mechanism comprising the air supplying path which is connected by switching means to the external path of the endoscope which is included in the water supplying system of the air and water supplying mechanism of the endoscope. The water left in the water supplying system can be positively discharged by the use of the supplied air after a portion of the body cavity has been examined with the endoscope. The supply path switching valve 5 and the valve 20 in the device according to these embodiments and the arrangement of the water supplying system can be changed and modified without departing the inventive concept of the invention.

In the embodiments of FIGS. 1 and 2 the pump 1 is employed for pressurizing the cleaning water to allow it to jet out of the top end part of the endoscope. Also, the switch 20 for the air supplying and the water supplying operation is provided in the manual operating section of the endoscope.

The switching device of this type is designed so that an air passing pipe for discharging the compressed air which is supplied through an air supplying pipe is provided, and when the outlet of the air passing pipe is closed, the compressed air is delivered into a pipe having the inner end at the top end part of the endoscope and the outer end communicating with the compressed air discharging path. Accordingly, when the air is being discharged through the air passing pipe, the pipe system is left open, which may cause the air in the body cavity to flow through the inner end of the pipe at the end portion of the endoscope or mucus in the body cavity to flow backwardly through the pipe.

In order to prevent this difficulty, the check valve 12 may be connected to the pipe system. However, this method is undesirable for sanitation, because dirt or the like is caught by the check valve, which makes it difficult to clean the pipe system.

Also, in such a device a pipe extending to the top end part of an endoscope is opened in a compressed air discharging path as described above, and if the operator, being ethusiastic for the observation, or the operation of the forceps, carelessly closes the outlet of the air passing pipe with his finger, then air is unintentionally delivered into the body cavity.

Furthermore, with the device, water is supplied to the endoscope by utilizing the pressure of compressed air with the outlet of the air passing pipe with the finger. Therefore, the outlet must be maintained closed with the finger throughout the water supplying operation, that is, the operator must pay attention to finger operation also, which may adversely affect the operation of the endoscope.

To overcome these difficulties a third embodiment of this invention are shown in FIGS. 3–12 which detail three examples of the air-water switching valve 20. In these embodiments the air valve switching mechanism 5 is eliminated and all control functions take place at the endoscope handle. In FIGS. 6–12 the valve is used for a metering function to adjust air pressure supplied to the body cavity.

FIG. 3 is an explanatory diagram showing the arrangement of a third embodiment of the invention. A cylinder 20 is arranged in the manual operating section body 3 of an endoscope. A piston assembly 30 is slidably fitted in the cylinder 20 in such a manner the top part 30a of the piston assembly is protruded from the cylinder 20 to depress the piston assembly 30. An air supplying pipe 4, a water supplying pipe 6, and an air and or water supplying conduit pipe 21 are connected to the cylinder 2. The pipe 21 extends to the top end part 60 of the endoscope. The other end of the air supplying pipe 4 is connected to an air pump 1 provided separately. The branch pipe 4a of the pipe 4 is inserted into a sealed cleaning water container 2. The other end of the water supplying pipe 6 is inserted into the cleaning water R in the container 1.

FIG. 4 is a vertical sectional view of the essential components of the first embodiment of the air-water valve according to the invention. The cylinder 20 is screwed into the manual operating section body 3 to form one unit. The air supplying pipe 4, the water supplying pipe 6 and the conduit pipe 21 are connected to predetermined portions (described later) of the wall of the cylinder, respectively. In this embodiment, the conduit pipe 21 is used to supply air and for water.

The piston assembly 30 comprises: a first piston 31 having a hollow part employed as an air passing pipe 80 for discharging compressed air, and a second piston 32 fitted over the first piston 31. That is, the piston assembly 30 is a dual concentric pipe. A spring 90 is disposed between the two pistons 31 and 32. More specifically, a locking ring 100 is provided at the lower end portion of the first piston 31 so that the second piston 32 is not removed from the first piston 31, under the action of the spring 9. That is, the first and second pistons are maintained in an ordinary state as shown in FIG. 2.

A pin 120 extending from the second piston is slidably fitted in an elongated groove 110 cut in the wall of the first piston 31, so that the first and second pistons are not turned relative to each other.

A finger placing part 31a serving as the outlet of the air passing pipe 80 is mounted on the top of the first piston 31. A side port 130 is formed in the lower portion of the first piston 31. The second piston 32 has a collar 32a at the upper portion thereof. A retaining fitting 140 is screwed into the body 3. A spring 90a having a relatively strong expanding force is interposed between the collar 32a and the retaining fitting 140. In this assembled condition, the second piston 32 is fitted into the above-described cylinder 20. A circumferential groove 150 and a small hole 150a connected thereto are formed in the wall of the second piston at a level coinciding with the piston of the end of the conduit pipe 21, which is opened in the wall of the cylinder when the lower end of the retaining fitting 140 abuts against the engaging shoulder 32b of the second piston 32.

A portion of the middle part of the second piston is removed to form a chamber 160 between the inner wall of the cylinder and the second piston. When the assembly of the two pistons 31 and 32 is inserted into the cylinder 20, in the ordinary state another chamber 170 is formed between the lower end of the assembly and the bottom of the cylinder 20.

The position of the end of the water supplying pipe 6, which is connection to the wall of the cylinder, is determined so that the pipe 6 communicates with the chamber 160. The end of the air supplying pipe 4, which is connected to the wall of the cylinder, is at a distance $l_2$ from the lower end of the second piston 32. This distance $l_2$ is the distance between the collar 32a of the second piston and the upper end of the retaining fitting 140. That is, it is the distance of movement of the second piston 32. The distance $l_2$ is employed for determining the positions of the ends of the conduit pipe 7 and the water supplying pipe 6, which are connected to the cylinder as shown in FIG. 4. The distance $l_1$ between the lower surface of the finger placing part 31a of the first piston 31 and the collar 32a, that is, the relative movement distance of the first and second pistons 31 and 32 is employed to determine the positions of the side hole 130 of the first piston 31 and the small hole 150a of the second piston 32.

In FIG. 4, reference character 180 designates watertight "O"-rings for purposes of sealing the unit.

In FIG. 5 shows a second example of the air-water valve according to the invention, in which those components which are similar in function to those described with reference to FIG. 4 are therefore similarly numbered.

In this embodiment, the piston section 30 is a single piston 33. A conduit pipe 21 connected to the cylinder 2 is used to supply air only, and a conduit pipe 190 for supplying water only is connected to the cylinder 20. A finger placing part 33a serving also as the collar described with reference to FIG. 4 is mounted on the top of the piston 33. The distance $m_1$ between the lower surface of the finger placing part 33a and a spring engaging member 220, that is, the first depression distance of the piston 33, is employed to determine the position of the end of a conduit pipe 21 supplying only air. The distance $m_2$ between the end of the wall of the finger placing part 33a and the locking shoulder of a retaining fitting 140, that is, the maximum movement distance of the piston 33 is employed to determine the positions of the ends of the air supplying pipe 4, the water supplying pipe 6, and the conduit pipes 21 and 190. In FIG. 5, reference character 33b designates a locking shoulder of the piston 33, which abuts against the lower surface of the retaining fitting 140.

Assembly of the devices described above can be achieved as follows: First, the cylinder 20 is screwed into the manual operating section body 3. Then, the pipes (4, 5, 21 and 190) are connected to the wall of the cylinder. The piston assembly 30 obtained by assembling its various components is inserted into the cylinder 20 and is secured fixedly by tightening the retaining fitting 140. Accordingly, if necessary, the piston assembly 30 can be readily removed from the cylinder 20, and accordingly from the body 3, by removing the retaining fitting 140.

In operation, when the air pump 1 is operated, air is supplied through the air supplying pipe 4 into the chamber 170 in the cylinder 30 and through the branch pipe 4a into the sealed container 2. However, since the water supplying pipe 6 extending from the container 2 is connected to the independent chamber 160 in the cylinder 20 (in the embodiment shown in FIG. 4) or it is closed by the piston 33 (in the embodiment shown in FIG. 5), therefore no air supplying operation is effecutated.

With respect to FIG. 4, the air supplied into the chamber 170 is discharged out of the outlet formed in the top part of the piston assembly 30 through the air passing pipe 80. In this case, the end of the conduit pipe 21 communicating with the top end part of the endoscope coincides with the circumferential groove 150 of the second piston 32, but the small hole 150a connected to the circumferential groove 150 is closed by the first piston 31. Therefore the end of the conduit pipe 21 is maintained closed.

Then, in order to supply air into the endoscope, the finger is placed on the finger placing part 31a while closing the outlet, and the finger placing part 31a is depressed by the finger. As a result, the first piston 31 is lowered, against the elastic force of the weak spring 90 disposed between the first and second pistons 31 and 32, the distance $l_1$ until the lower surface of the finger placing part 31a abuts against the upper surface of the collar 32a. As a result, the side hole 130 of the first piston 31 coincides with the small hole 150a of the second piston 32, so that the conduit pipe 21 is in communication with the air passing pipe 80. Accordingly, the air supplied through the air supplying pipe 4 is delivered through the conduit pipe 21 and is jetted out of the top end part 60 of the endoscope, since the outlet of the air passing pipe 80 has been closed by the finger.

When the piston assembly 30 is further depressed, then the second piston 32 integral with the first piston 31 is lowered, against the elastic force of the strong spring 90a, the distance $l_2$ until the lower surface of the collar 32a abuts against the upper surface of the retaining fitting 140. As a result, the chamber 160 is also lowered, and accordingly the water supplying pipe 6 is in communication through the chamber 160 with the conduit pipe 21, while the air supplying pipe 4 is closed by the second piston 32.

Accordingly, compressed air is delivered from the air pump 1 through the branch pipe 4a into the sealed container 1. As a result the pressure created in the container 1 is applied to the cleaning water R therein, so that the cleaning water is delivered through the air supplying pipe 6 and the conduit pipe 21 communicating therewith to the top end part 60 of the endoscope, thus being ejected out of it.

When the finger is removed from the piston assembly 30, the first and second pistons 31 and 32 are returned to their initial positions by the elastic forces of the springs 90 and 90a to suspend the above-described operation.

In the case of the fourth embodiment shown in FIG. 5, by the first depression of the piston 33, the piston 33 is moved the distance $m_1$ against the elastic force of the weak spring 90. Under this condition, the conduit pipe 21 for supplying air only communicates through the circumferential groove 150 to the air passing pipe 80. In this case, since the outlet in the finger placing part has been closed by the finger, the air supplied through the air supplying pipe 4 is ejected out of the top end part 60 of the endoscope.

When the piston 33 is further depressed the distance $m_2$, then similarly as in the third embodiment shown in FIG. 4, the conduit pipe 190 for only supplying air communicates through the chamber 160 with the air supplying pipe, so that water is delivered to the top end part 60 of the endoscope.

As is apparent from the above description, with respect to the means of switching the water and air supplying operations in the device according to the invention, in the ordinary state thereof, i.e., before the valve is operated, the ends of the conduits connected to the cylinder are closed by the piston. Therefore, it is possible to prevent air or dirt from flowing backwardly into the conduits due to the pressure in the body cavity. Thus, the conditions of observation can be maintained in a stable environment. The amount of air supplied into the body cavity is limited to a minimum value necessary for the observation, which relieves discomfort to the patient.

The device itself is not contaminated by dirt or the like, that is, it is kept sanitary, which is effective to protect a patient from infection. In the ordinary state in which no air and water supplying operations are carried out, the conduits for supplying air and water are closed. Therefore, even if the operator closes the outlet formed in the top part of the piston carelessly during the observation, no air is supplied to the top end part of the endoscope. Hence according to these examples the device is excellent in terms of security of operation. Furthermore, in the water supplying operation in which the piston is depressed, the air supplying pipe connected to the cylinder is closed by the piston. Therefore, in this case, it is unnecessary to continuously close the aforementioned outlet of the air passing pipe with the finger. Accordingly, the burden on the operator to pay attention to the operation of the finger can be relieved.

Referring now to FIGS. 6-11 a third example of an air-water valve is shown in which the air pressure can be precisely controlled.

FIG. 6 is a vertical sectional view showing the essential components of an air and water supplying device according to the third example of this invention. A cylinder 20 is fixedly screwed into the manual operating section 3 of an endoscope. A piston 30 is slidably fitted into the cylinder 20 in such a manner that it can be readily depressed downwardly but it cannot be removed from the cylinder by means of a retaining fitting 140. An annular collar 160 retained by a locking washer 250 is slidably fitted over the piston 30. A weak elastic spring 90a is interposed between the collar 260 and the shoulder of the retaining fitting 140, and a strong elastic spring 90 is interposed through the locking ring of an adjusting member (described later) between the collar 260 and the locking edge 30a of the piston 30.

A mechanism for preventing the rotation of the piston 30 is provided between the cylinder 20 and the piston 30. It comprises, a pin 190 extending from the cylinder 20 into a long groove 30b cut axially in the lower portion of the piston 30. A conduit pipe 21 communicating with the top end part 60 of the endoscope, an air supplying pipe 4 connected to an air pump 1 and a water supplying pipe 6 connected to a water storing tank 2 are connected to the side wall of the cylinder 20. The positions of connection of the conduit pipe 21, the air supplying pipe 4 and the water supplying pipe 6 are as follows: The air supplying pipe 21 is connected to a point on the side wall of the cylinder, which is below the lower end of the piston 30 when the piston 30 is positioned as indicated in FIG. 6 by the elastic forces of the two springs 90 and 90a and which is above the lower end (indicated by the dotted line) of the piston when the piston 30 is depressed. The air supplying pipe 6 is connected to the side wall so that it is at all times in communication with a chamber 160 which is formed by the inner wall of the cylinder 20 and a recess cut in a portion of the outer wall of the piston 30. The conduit pipe 21 is connected to a point on the side wall of the cylinder, which coincides with a side hole 150 cut in the piston 30 when the piston 30 is slightly depressed, and communicates with the above-described chamber 160 when the piston 30 is further depressed. A through-hole, or an air discharging path 80, is cut along the axis of the piston 30. Thus, the piston 30 is utilized as an air discharging pipe. Outlets 27a, 27b, and 27c are formed radially in the upper portion of the piston 30 so that these outlets communicate with the air discharging path 80 in the piston 30 (cf. FIGS. 7 through 10).

Furthermore, an adjusting member 280 is rotatably fitted over the top end portion of the piston 30 by being positioned by a finger placing member 31a and the locking ring 280a. The adjusting member 280 as shown in FIGS. 7 through 10, has grooves 290a, 290b, 290c and 290d varying in circumferential length which are cut in its inner peripheral wall adjacent to the piston 30, and through-holes 220a, 220b, 220c and 220d communicating respectively with the grooves 290a, 290b, 290c and 290d, which are cut in the outer peripheral wall of the cylinder 20 at a level equal to that of the above-described outlets 27a through 27c.

The piston 30 has engaging grooves 221a, 221b, 221c and 221d in the outer wall (FIG. 11) which are positioned in association with the positions of the outlets 27a through 27c and the grooves 290a through 290d. A threaded pipe 24 is screwed in the wall of the adjusting member 280, and a click ball 23 is placed in the threaded pipe and is energized by a spring 22 so that it can engage with the above-described engaging grooves 221a through 221d. Furthermore, an engaging pin 26 is screwed in the wall of the adjusting member 280 in such a manner that its end portion protrudes in a rotation regulating groove 25 cut in the outer wall of the piston 30.

In FIG. 6, reference character 240 designates abutting pins protruded from the retaining fitting 140 toward the abutting shoulder of the piston 30, and reference numeral 180 designates "O"-rings fitted in the piston 30.

FIG. 12 is a graphical representation indicating characteristic curves $L_1$ and $L_2$ representative of the relationships between the area D of the outlet of the air discharging pipe of the device according to this invention and the air supplying pressure P, and between the area D and the air supplying quantity Q.

First, the device is in a normal state as shown in FIG. 6. That is, the piston 30 is at the upper position where it is pushed upwardly by the elastic forces of the springs 90 and 90a but is retained by the abutting pins 240 of the retaining fitting 140. In this condition, air is introduced into the cylinder 20 through the air supplying pipe 4 by the operation of the air pump 1. However, since the conduit pipe 21 is closed by the piston 30, the air is not delivered to the top end part 60 of the endoscope. Furthermore, the water supplying pipe 6 communicates with the independent chamber 160, but not with the conduit pipe 21, and therefore no air or water is supplied to the top end part 60 of the endoscope.

If, under this condition, the piston 30 is depressed, first the piston 30 is lowered against the elastic force of the weak spring 90a while compressing the latter. This depression is continued smoothly until the annular collar 260 supporting one end of the spring abuts against the shoulder of the retaining fitting 240, i.e., the depressing finger feels the reaction which is caused when the succeeding depression causes the annular collar 260 to compress the strong spring 90.

In this first step of depressing the piston, the air supplying pipe is maintained in communication with the air discharging path 80 and the conduit pipe 21 coincides with the side hole 150 of the piston 30. Therefore, the air delivered through the air supplying pipe 4 is introduced into the conduit pipe 21 and is delivered to the top end portion 60 of the endoscope.

In this case, the rotation of the piston 30 is prevented by the pin 190 inserted in the wall of the cylinder 20 and the adjusting member 280 has been turned so that the positional relation between the grooves 290a through 290d and the outlets 27a through 27c of the piston 30 is one of those shown in FIGS. 7 through 10.

When the outlets 27a through 27c are not in communication with the grooves 290a through 290d as shown in FIG. 7, air is supplied to the top end part of the endoscope through the air supplying pipe 4 under a high pressure.

When the outlet 27a coincides with the groove 290a but the remaining outlets 27b and 27c are closed as shown in FIG. 7, air is supplied to the top end part 60 of the endoscope with the air supplying pressure being regulated, or reduced, according to the opening areas of the outlet 27a and the through-hole 220.

When two or three of the outlets 27a through 27c communicate with the grooves 290a through 290d as shown in FIG. 9 or 10, air is supplied to the top end part 60 of the endoscope under the condition that the air supplying pressure is reduced according to the sum of the opening areas of the outlets communicating with the grooves.

The setting of communication of the outlets 27a through 27c is held by the click ball 23 which is selectively engaged with the engaging grooves 221a through 221d within the range of rotation of the adjusting member 280 which is defined by the rotation regulating groove 25 and the engaging pin 26.

The air is supplied to the top end part 60 of the endoscope under the various pressures which are defined by the various setting positions of the adjusting member varied as indicated by the characteristic curve $L_1$ in FIG. 12. In FIG. 11, Q is the sum of the opening areas of the outlets communicating with the grooves, and $P_1$ is the air pressure when all of the outlets are closed. In response to the variations of the air pressure P, the air supplying quantity Q at the top end part 60 of the endoscope is varied as indicated by the characteristic curve $L_2$, where $Q_1$ is the air supplying quantity when all of the outlets are closed. Accordingly, the air supplying pressure P and the air supplying quantity Q per unitary time can be relatively accurately controlled by adjusting the sum of the opening areas of the outlets 27a through 27c. Accordingly, air can be supplied under a suitable pressure to a portion of the body cavity to be examined. A suitable amount of air can be delivered to a desired portion of the body cavity by reducing the air supplying pressure after a certain amount of air has been supplied under a high pressure. In this case, the condition of the portion to be examined can be dynamically observed with ease.

In the case where water is supplied to the top end part of the endoscope, the piston 30 depressed to the air supplying position thereof is further depressed. As a result the piston 30 is lowered against the elastic force of the strong spring 90 while compressing the latter. When the piston 30 is depressed to its lower-most position, the chamber 160 is also moved downwardly. Therefore, the conduit pipe 21 communicates through the chamber 160 with the water supplying pipe 6, while the air supplying pipe 4 opened in the cylinder is closed by the piston 30 thus depressed. Accordingly, irrespective of the setting condition of the outlets 27a through 27c, the high pressure P is applied to the water storing tank 2 by the air pump 1. As a result, cleaning water in the tank 2 is elevated through the water supplying pipe 6 and is ejected out of the top end part 60 of the endoscope.

If the depression position of the piston 30 is released, the piston 30 is returned to its initial position by the elastic forces of the springs 90 and 90a. Therefore, the supply of water or air can be suspended by releasing the piston 30 at any time.

In this third example of the air and water supplying device described above, the path 80 for discharging the air supplied into the cylinder from the air supplying pipe 4 is provided in the piston 30. However, the device may be modified so that a pipe for discharging air only which is connected to the bottom of the cylinder 20 is used instead of the air discharging path 80. In this case, the outlets 27a through 27c and the adjusting member 280 should be provided for this pipe. Furthermore, in the above-described example of the device according to the invention, the adjusting member 280 is turned for adjusting the conditions of air; however, it may be so designed that it is slid for the same purpose within the scope of the invention.

As is apparent from the above description, in the air and water supplying device according to this embodiment, single or plural outlets are provided for the air discharging pipe in such a manner that the sum of the opening areas of these outlets is adjusted by the adjusting member. Therefore, an air supplying pressure and an air supplying quantity per unitary time suitable for a portion of the body cavity to be examined can be readily obtained. Accordingly, the discomfort to a patient can be eased, and it is possible to positively protect a patient from danger. In addition, the condition of the portion to be examined can be dynamically observed. Thus, the portion to be examined can be precisely observed and diagnosed.

Figure 13:
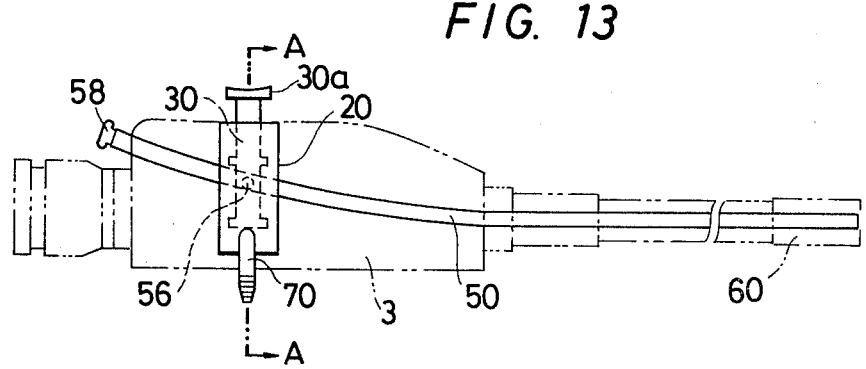
FIG. 13 is a side view showing an example of a suction valve according to this invention incorporated in the manual operating section of an endoscope.
Figure 14:
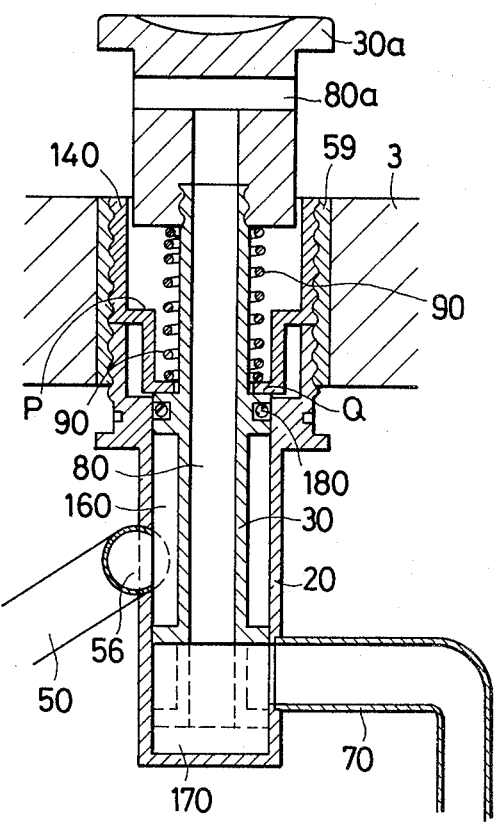
FIG. 14 is a sectional side view taken along line A—A in FIG. 1, showing the valve according to the invention.

FIGS. 13—15 show a valve used for control of suction in accordance with this invention.

FIG. 13 is a side view showing a suction device according to the invention assembled with the manual operating section body of an endoscope. A piston 30 is fitted in a cylinder 20 incorporated in the manual operating section body 3, such that the piston 30 can be freely depressed and the top part 30a of the piston 30 protrudes from the cylinder 20. A bioptic instrument introducing pipe 50 has the inner end opened in the top end part 60 of the endoscope, and the outer end protrudes outside the body 3. The pipe 50 is provided with a side hole 56 which is connected to the side wall of the cylinder 20 so that the pipe 50 communicates therewith. A suction pipe 70 connected to an air sucking pump (not shown) is connected to the side wall of the cylinder 20 so that the pipe 70 communicates therewith. In FIG. 13, reference numeral 58 designates a plug adapted to close the outer end of the pipe 50.

FIG. 14 is an enlarged sectional view taken along line A—A in FIG. 13, showing the valve according to the invention. The cylinder 20 is screwed into a mounting ring 59 embedded in the manual operating section body 3. The piston is inserted into the cylinder, and the cylinder 20 is retained in place by means of a retaining fitting 140. Thus, the cylinder 20 and the body 3 form one unit. The above-described side hole of the introducing pipe 50 and the air sucking pipe 70 are connected to different portions of the cylinder 20 so that the pipes 50 and 70 communicates with the cylinder 20.

An air passing pipe 80 is formed by cutting the axial portion of the piston 30 except for the finger placing portion of the top part 30. In the top part 30a, a port 80a is formed perpendicularly to the air passing pipe 80 in such a manner that the port 80a communicates with the air passing pipe 80. A portion of the outer wall of the piston 30, which slides along the cylinder 20, is cut to form a first chamber 160 with the inner wall of the cylinder 20. A second chamber 170 is formed by the inner end of the piston 30, the bottom of the cylinder 20 and the inner wall of the cylinder 20 in such a manner that it communicates with the air passing pipe 80. The side hole 56 of the introducing pipe 50 is connected to the side wall of the cylinder forming the first chamber 160.

The air sucking pipe 70 is connected to the side wall of the cylinder in such a manner that it communicates with the second chamber 170 when the piston 30 is placed at the upper position by the elastic force of the spring 90, and it communicates with the first chamber 160 when the piston 30 is depressed against the elastic force of the spring 90.

In FIG. 14, reference characters P and Q designates a piston depression position regulating abutting surface and a piston protrusion position regulating abutting surface which are formed by bending the retaining fitting 140, respectively. Reference numeral 180 designates an air-tight "O"-ring provided for the piston 30.

Figure 15A:
FIGS. 15A and 15B are an explanatory diagrams showing different examples of one end of an air sucking pipe of the device according to the invention, which is opened in the wall of the cylinder.
Figure 15B:
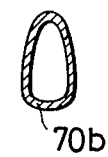

FIGS. 15A and 15B show examples of the opening end of the air sucking pipe 70, which is connected to the cylinder 20. The configuration of the end of the pipe 70A, shown in FIG. 15(A) is substantially circular, while the configuration of the end of pipe 70B shown in FIG. 15(B) is of a deformed circle, the width of the opening being shorter in the upper portion than in the lower portion.

In the device according to the invention as described above, the side holes 56 of the bioptic instrument introducing pipe 50 and the air sucking pipe 70 are connected in advance of operation to the cylinder 20 fixedly secured to the mounting ring 59 of the manual operating section 3. Then, the piston 30 is inserted into the cylinder 20, and the retaining fitting 140 is screwed into the mounting ring 59 to fixedly secure the cylinder 20. While the piston is prevented from falling off, the spring 90 is placed on the lower shoulder of the retaining fitting 140, and then the top part 30a is engaged with the upper end portion of the piston 30. Thus, the assembly of the device has been completed.

However, the assembling of the device may be achieved in accordance with the following alternate method: First, the retaining fitting 140 is inserted into the mounting ring 59. Thereafter, the spring 90 is placed on the lower shoulder of the retaining fitting 140. In this condition, the top part 30a is connected to the upper portion of the piston 30. Then, the retaining fitting 140 is tightened.

Accordingly, in cleaning the device after use or in replacing the piston 30, the piston 30 can be readily removed from the cylinder 20 by removing the fitting 140.

The device thus constructed is in a state ready for the start of use; that is, the piston 30 is at the upper position by the elastic force of the spring 90 as shown in FIG. 14. In this condition, an external air sucking path comprising the air sucking pipe 70 opened in the second chamber 170, the second chamber 170, the air passing pipe 80 and the port 80a is formed. This occurs while the bioptic instrument introducing pipe 50 communicates through its side hole 56 with the first chamber 160 separated from the second chamber 170. Accordingly, no air sucking operation is effectuated for the body cavity by the air sucking pump.

A bioptic instrument such as forceps is inserted into the bioptic instrument introducing pipe 50 in such a manner that its outer end is tightly closed thereby. In the portion of the pipe 50 in which the bioptic instrument is inserted, there is a space between the bioptic instrument inserted and the wall of the pipe 50 sufficient to suck mucus. When a bioptic instrument is not inserted into the pipe 50, the outer end of the pipe 50 is closed by the plug 58.

If the top part 30a of the piston 30 is depressed against the elastic force of the spring 90 to lower the piston 30, then the lower end of the piston 30 is lowered to the position indicated by the dotted line in FIG. 14, while the first chamber 160 is also lowered. As a result, the pipe 50 communicates through the first chamber 160 to the air sucking pipe 70. Therefore, the suction force of the air sucking pump acts on the side hole 56 of the pipe 50 through the air sucking pipe and the first chamber 160 to thereby suck mucus, etc. from the body cavity.

The range of suction by depressing the piston 30 is limited by the abutting surface P against which the inner end of the top part 30a of the piston abuts as the piston 30 is depressed. As the piston 30 is lowered by the depression of its top part 30a, the lower end of the piston is caused to cross the opening 70a or 70b of the air sucking pipe 70, that is, the air sucking pipe 70 is gradually shifted from the second chamber 170 to the first chamber 160. Accordingly, the suction force in the side hole 56 and accordingly in the introducing pipe 50 is controlled according to the amount of depression of the piston 30.

As is apparent from the above description, in the valve according to this embodiment of the invention, the two separate chambers are formed by the cylinder and the piston slidably inserted thereinto, and communicate with the sucking pipe, and the air sucking pipe and the air passing pipe, respectively. As the piston is depressed, the first chamber is moved downwardly to switch the above-described communication states; that is, the air passing tube is disconnected from the air sucking pipe 70, while the sucking pipe communicates with the air sucking pipe 70 through the first chamber. Accordingly, unlike the conventional device, it is unnecessary to close the opening of the air passing pipe with the finger.

According to this embodiment, the suction operation becomes ready merely by lightly placing the finger on the top of the piston. Therefore, operator fatigue is reduced during operation, and undesirable suction which may be caused by carelessly closing the end of the air passing tube with the finger can be eliminated. Unlike the conventional device in which the end of the air passing tube is closed with the finger, the communication condition of the sucking pipe and the air sucking pipe can be gradually shifted to the complete communication condition by controlling the amount of depression of the piston and the range of depression being relatively large. By this operation, the gas in the body cavity can be sucked at a described rate, slowly or quickly.

Accordingly, a portion of the body cavity to be examined can be dynamically observed while being expanded. In the case where air is excessively supplied into the body cavity, the air can be removed at a desired rate, and therefore the patient will not be made uncomfortable.

In the case when the bioptic instrument introducing pipe of the device according to the invention is used as a sucking pipe, it is possible to open widely the communication opening thereof to the extent that only a part of the wall of the introducing pipe is in the chamber, because the sucking tube is designed so that it communicates with one of the chambers. Thus, the suction power can be increased without obstructing the insertion of the bioptic instrument into the pipe. This is a secondary effect of the invention.

The air passing pipe of the device of the invention is of normally open type that needs no external operation such as closing the end thereof. Therefore, it is not always necessary to form the air passing pipe as a through-hole in the piston as in the above-described example. That is, an air passing pipe may be provided so that it is extended from an opening formed in the bottom of the cylinder to the outside of the instrument housing. In the example described above, the bioptic instrument introducing pipe is employed as the sucking pipe; however, a pipe for suction only may be employed according to the invention. In this case, one end of this pipe can be connected directly to a predetermined portion of the wall of the cylinder for more effective results.

While the invention has been described with respect to various embodiments it is apparent that modifications can be made without departing from the essential scope thereof.

What is claimed is:

1. A device for switching air and water supplying operations in an endoscope, comprising;
  a cylinder (20) arranged in the manual operation section body of said endoscope;
  piston means slidably inserted into said cylinder, the top part of said piston means protruding from said manual operation section body so that said piston means can be freely disposed to a plurality of positions, said cylinder and piston means forming first (160) and second (170) separate chambers in said cylinder;
  an air passage pipe (80) having an outlet in the top portion of said piston means;
  at least one conduit pipe (21) communicating with an end part of said endoscope;
  an air pump and an air supplying pipe connected to said air pipe; and
  a water supplying pipe;
  said conduit pipe, said air supplying pipe and said water supplying pipe being connected to said cylinder such that said air supplying pipe and said air passage pipe are in communication through said second chamber when said piston means is in a first of said plurality of positions, said first position defined by the absence of external depression forces on said piston means, said conduit pipe being closed to communication with said first and second chambers by said piston means in said first position; said conduit pipe being in communication with said air passing pipe and air supplying pipe when said piston means is in a second of said plurality of positions physically displaced from said first position, said water supplying pipe being in communication through said first chamber with said conduit pipe when said piston means is in a third of said plurality of positions physically displaced from said first and second positions, said air supplying pipe being closed to communication to said second chamber by said piston means in said third position.

2. A device as in claim 1 wherein a conduit pipe for supplying only air and a conduit pipe for only supplying water, or a conduit pipe for supplying air and/or water is employed.

3. A device as in claim 1, wherein said piston means comprises first and second pistons, said second position produced by moving said first piston relative to said second piston, and said third position produced by moving said first and second pistons relative to said cylinder.

4. A device as in claim 1 further comprising means to effectuate removal of said piston from said cylinder.

5. A device as in claim 3 further comprising means to bias said first piston relative to said second piston and means to bias said second piston relative to said cylinder.

6. The device as in claim 5, further comprising collar means to limit the depression of said piston means into said cylinder to said third position whereby said water supply pipe is in communication with said conduit pipe.

7. The device as in claim 1, 2, 3 or 4 wherein said outlet in the top part of said piston means is adapted to be selectively opened and closed by the finger of the endoscope operator.

* * * * *